United States Patent [19]

Gardocki

[11] 4,338,324
[45] Jul. 6, 1982

[54] ANALGESIC POTENTIATION

[75] Inventor: Joseph F. Gardocki, Doylestown, Pa.

[73] Assignee: McNeilab, Inc., Fort Washington, Pa.

[21] Appl. No.: 244,562

[22] Filed: Mar. 17, 1981

[51] Int. Cl.³ .................... A61K 31/40; A61K 31/455
[52] U.S. Cl. ..................................... 424/266; 424/274
[58] Field of Search ................................ 424/266, 274

[56] References Cited

U.S. PATENT DOCUMENTS 4,233,313 11/1980 Gardocki ............................ 424/274
4,233,317 11/1980 Gardocki ............................ 424/317
4,234,601 11/1980 Gardocki ............................ 424/319

OTHER PUBLICATIONS

Physician's Desk Reference, 34th Ed. (1980), pp. 730–731.
Cooper, S. A., J. Clin. Pharmacol., 20(4), Part 2, 230 (1980).
Wallenstein, S. L. et al. J. Clin. Pharmacol. 20(4) Part 2, 250 (1980).
Gilbert, M. M. et al., J. Int. Med. Res., 6, 14–23 (1978).
Levin, H. M. et al., J. Int. Med. Res., 6 24–33 (1978).

*Primary Examiner*—Stanley J. Friedman

[57] ABSTRACT

The analgesic effect of zomepirac is potentiated by simultaneously or sequentially administering to a subject suffering from pain, butorphanol, in a nonanalgesic amount thereby significantly reducing the dosage of zomepirac.

7 Claims, No Drawings

ANALGESIC POTENTIATION

This invention is directed to improved methods and compositions for producing analgesia with combinations of butorphanol and zomepirac which have a potentiating effect on zomepirac.

BACKGROUND OF THE INVENTION

One of the long existing primary goals of medicine is the relief of pain. Relief is sought most generally by the administration of analgesic drugs which produce a state of decreased awareness of the sensation and increase of the pain threshold.

Almost all potent analgesics evoke reactions other than the relief of pain. Some of the reactions are gastrointestinal disturbances, nausea, constipation and vomiting. Among the more serious of the side reactions and one frequently found in analgesic drugs is respiratory depression. Thus, in the use of anlagesics in man, considerations other than the primary effect (analgesia), must be made and drugs for pain relief are sought which have maximum analgesic effect accompanied by minimum side reactions. It is difficult to satisfy these requirements with a single chemical entity since generally a potent analgesic has accompanying serious side reactions while a drug with little or no side effects is generally less effective as an analgesic.

Thus, there is a continuing search for a combination of two or more drugs whereby the total quantity of drug can be reduced and which can be employed in such proportions as to produce maximum analgesic effect with little or no side effects. When one or both of the components of a combination is known to possess pain-relieving properties, but these properties are increased many fold over that which would be expected by simple addition of these properties, the net effect of the combination is commonly referred to as "potentiation".

It has now been found that the analgesic effect of zomepirac is potentiated by butorphanol.

Zomepirac is the generic name for 5-(4-chlorobenzoyl)-1,4-dimethyl-1H-pyrrole-2-acetic acid represented by the formula;

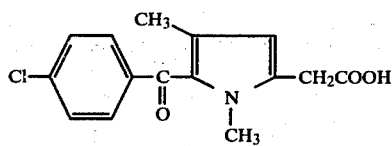

Zomepirac is useful as an analgesic agent either in its acid form or as a pharmaceutically acceptable salt thereof. The pharmaceutically acceptable salts are those obtained from appropriate organic or inorganic bases. Preferred salts include the sodium and potassium salts. Zomepirac is commercially available in the form of a salt thereof as zomepirac sodium, which is the generic name for sodium 5-(4-chlorobenzoyl)-1,4-dimethyl-1H-pyrrole-2-acetate dihydrate.

Butorphanol is the generic name for 17-(cyclobutylmethyl)morphinan-3,14-diol or levo-N-cyclobutylmethyl-3,14-dihydroxymorphinan. It can be used as such or in the form of a pharmaceutically acceptable salt, preferably of a weak organic acid such as tartaric acid.

Butorphanol is recognized as an analgesic agent with useful antinociceptive properties. However, in certain instances it may produce sedation, psychotomimatic and dysphoric effects. The effect of the combination of these drugs on the analgesic properties was not known prior to our work.

STATEMENT OF THE INVENTION

The present invention concerns an improved method of producing analgesia made possible by the discovery that a potentiation of analgesic or antinociceptive properties of zomepirac is produced by a combination of zomepirac and butorphanol is specific proportions, the amount of butorphanol being less than that which would produce an analgesic effect if administered alone. The efficacy of the combination in the suppression of pain is unexpectedly much greater than that which would result from simply the additive effects of the components. While butorphanol potentiates the analgesic effect of zomepirac, zomepirac does not serve to potentiate the analgesic effect of butorphanol.

The present invention also concerns the composition containing both zomepirac and butorphanol which is used in the above method.

DESCRIPTION OF THE INVENTION

The novel and unexpected superior analgesic properties may be achieved by the simultaneous or sequential oral, or parenteral and oral administration of (1) butorphanol or a pharmaceutically acceptable salt thereof (preferably in the form of its tartrate salt), and (2) zomepirac or a pharmaceutically acceptable salt thereof. The pharmaceutically acceptable salts are those obtained from appropriate organic or inorganic bases. Preferred salts include these of sodium, potassium and the like.

The present invention thus involves a method for producing analgesia by administering to a subject suffering from pain zomepirac or a pharmaceutically acceptable salt thereof as the primary agent and butorphanol or a pharmaceutically acceptable salt thereof as the potentiating agent. As will be explained, both agents may be administered orally, in which case the composition used contains from about 5.63 to 100 milligrams of zomepirac and 0.31 to 5.42 milligrams of butorphanol (although the two agents may also be administered separately, either simultaneously or sequentially). In terms of milligrams per kilogram of body weight, the amounts used are from about 0.080 to 1.43 of zomepirac and 0.0044 to 0.0774 of butorphanol. The butorphanol, and zomepirac if desired and available may also be administered parenterally. When the butorphanol is administered parenterally, and the zomepirac orally, the amounts used to obtain the potentiation differ slightly. In that case, the zomepirac primary agent is administered orally at a dosage of about 9.6 to 100 milligrams or 0.140 to 1.43 mg/kg of body weight, while the butorphanol potentiating agent is administered parenterally (preferably intramuscularly) at a dosage of about 0.105 to 2.0 milligrams or 0.0028 to 0.029 mg/kg of body weight. As will be shown, the dosage range for the primary agent in a subject suffering from pain is significantly reduced by a relatively small amount of the potentiating agent.

The efficacy of the novel combination in producing antinociceptive properties is particularly seen in the acetylcholine bromide abdominal constriction response assay of Collier et al. [Brit. J. Pharmacol. Chemotherap., 32, 295–310 (1968)] sometimes referred to as the "mouse writhing test". In this test, mice are dosed with a test drug combination and thereafter injected intraperitoneally with acetylcholine bromide and the abdominal constriction responses or block of the abdominal constriction responses are observed and compared with control operations.

More specifically, in the operation carried out substantially as described by Collier and co-workers nonfasted male albino mice weighing 18–24 grams were dosed with combinations of one test drug in selected fixed doses (Drug A) together with a second test drug (Drug B) at variable doses for each fixed dose of Drug A. These were compared with animals dosed with (a) the first test drug (Drug A) at the same doses used in combination but employing saline instead of the second drug (Drug B), (b) the second test drug (Drug B) at doses used in combination but employing saline instead of the first drug, and (c) a saline control containing no drug. Each of the fixed doses Drug A employed were found to be inactive in the acetylcholine bromide abdominal constriction response assay at those dose levels.

In carrying out the test, the test compositions and the control compositions both with and without drugs were administered orally or orally and subcutaneously to the test mice. After about 30 minutes, the mice were injected intraperitoneally with acetylcholine bromide and the abdominal constriction responses compared corrected for saline responses as necessary.

When the percent block of abdominal constriction observed with the fixed dose (Drug A) was 5 percent or more, the percent block observed with each of the combination dosage levels was corrected with respect to the percent block observed with a fixed dose drug using Abbott's formula for natural mortality.

Likewise when the response to acetylcholine bromide in the saline control group was 95 percent or less, the response observed with each of the variable dosage levels plus saline was similarly corrected using Abbott's formula for natural mortality. $ED_{50}$ and 95 percent confidence limits were calculated using Finney's probit analysis procedure [Finney, D. J., 1964. *Probit Analysis*, Second Edition, University Press, Cambridge]. Following a test for parallelism, $ED_{50}$'s for a given comparison were calculated using a common slope where the slopes of the curves were not significantly different; otherwise they were calculated individually.

Employing the above procedures, potentiation of the analgesic properties of a zomepirac compound by a butorphanol compound may be demonstrated. This potentiation effect is illustrated employing zomepirac (sodium salt) and butorphanol (tartrate salt) but it is understood that it is not limited thereto but applies to the nonsalt form or to other pharmaceutically acceptable salts as well.

Nonfasted male albino mice weighing 18–24 grams were dosed per os (p.o.) with zomepirac sodium at various doses and with saline and with zomepirac sodium at various doses and a fixed dose of butorphanol tartrate either subcutaneously (sc) or orally. The fixed doses of butorphanol tartrate administered subcutaneously were 0.01, 0.025 and 0.05 mg/kg as seen in Table I. The fixed doses of butorphanol tartrate administered orally were 0.05, 0.14, 0.25, and 0.44 mg/kg as seen in Table II. Twenty mice were employed for each dosage level. As controls, a similar number of mice were dosed with butorphanol tartrate (0.01 mg/kg sc) plus saline (5 ml/kg p.o.), (0.025 mg/kg sc) plus saline (5 ml/kg p.o.), 10.05 mg/kg sc plus saline (5 ml/kg p.o.) and a double dose of saline (5 mg/kg sc) plus saline (5 mg/kg p.o.) [Table I]. Controls for the experiments where zomepirac sodium and butorphanol tartrate were both administered orally [Table II] consisted of butorphanol tartrate plus saline as follows. (0.05 mg/kg p.o.) plus saline (5ml/kg p.o.), (0.14 mg/kg p.o.) plus saline (5 ml/kg p.o.), (0.25 mg/kg p.o.) plus saline (5 ml/kg p.o.) or (0.44 mg/kg p.o) plus saline (5 ml/kg p.o.) and a double dose of saline (10 mg/kg p.o.). Zomepirac sodium was administered in aqueous solution. Butorphanol tartrate was administered in aqueous solution. (Where "mg/kg" or "ml/kg" is employed, "kg" is in reference to body weight).

Thirty minutes after administration of zomepirac sodium and butorphanol tartrate, the mice were injected intraperitoneally with 5.5 mg/kg of acetylcholine bromide and observed for the presence or absence of the abdominal constriction response. $ED_{50}$ values were determined from the observed values applying where pertinent corrections previously discussed. The results are seen in Tables I and II.

Evidence of the fact that butorphanol tartrate actually potentiates the analgesic potency of zomepirac sodium is based on the laboratory observation that inactive doses of butorphanol tartrate in the analgesic assay can significantly lower the oral analgesic $ED_{50}$ for zomepirac sodium. This lowering of the oral analgesic $ED_{50}$ of zomepirac sodium was observed when butorphanol tartrate was administered subcutaneously at doses of 0.025 and 0.05 mg/kg. Where potentiation does not occur the two $ED_{50}$'s for zomepirac sodium are not significantly different one from the other $p > 0.05$ in Table I as in the case where a dose of 0.01 mg/kg of butorphanol tartrate was administered subcutaneously.

The minimal subcutaneous dose of butorphanol tartrate that would be expected to significantly potentiate the oral analgesic potency of zomepirac sodium was estimated graphically. As can be seen from the data in Table I, the subcutaneous administration of 0.01 mg/kg of butorphanol tartrate did not result in a significant increase in the potency of zomepirac sodium (potency increase 1.11 fold) and a significant increase in the potency of zomepirac sodium was observed when a dose of 0.025 mg/kg of butorphanol tartrate was administered, (2.61 fold increase). In view of the foregoing relationship it is assumed that if the potency of zomepirac sodium were increased two-fold, the difference between the calculated $ED_{50}$ for zomepirac sodium plus saline and the calculated $ED_{50}$ for zomepirac sodium plus butorphanol tartrate would be significant at the 5 percent level. The theoretical dose of butorphanol tartrate that would be expected to affect a significant increase in the potency of zomepirac sodium, two-fold increase, was estimated graphically from a plot of the potency increases of 1.11 and 2.61 versus the doses of butorphanol tartrate employed. The dose of butorphanol tartrate thus estimated is 0.0195 mg/kg. Since the dose of 0.025 mg/kg of butorphanol tartrate administered subcutaneously did not produce a significant analgesic effect when administered with saline it is also expected that the lower dose of 0.0195 mg/kg would not produce a significant analgesic effect in this assay.

TABLE I

| Treatment | Zomepirac $ED_{50}$ (95% CL) mg/kg p.o. | Potency ratio |
|---|---|---|
| Zomepirac plus saline | | |

TABLE I-continued

| Treatment | Zomepirac ED$_{50}$ (95% CL) mg/kg p.o. | Potency ratio |
|---|---|---|
| 5 ml/kg sc | 0.71 (0.49–1.03) | |
| Zomepirac plus butorphanol 0.05 mg/kg sc | 0.38 (0.26–0.54)* | 1.87 |
| Butorphanol 0.05 mg/kg sc plus saline 5 ml/kg p.o. | Inactive | |
| Zomepirac plus saline 5 ml/kg sc | 0.73 (0.51–1.04) | |
| Zomepirac plus butorphanol 0.025 mg/kg sc | 0.28 (0.19–0.41)* | 2.61 |
| Butorphanol 0.025 mg/kg sc plus saline 5 ml/kg p.o. | Inactive | |
| Zomepirac plus saline 5 ml/kg sc | 0.70 (0.50–0.98) | |
| Zomepirac plus butorphanol 0.01 mg/kg sc | 0.63 (0.43–0.91) | 1.11 |
| Butorphanol 0.01 mg/kg sc plus saline 5 ml/kg p.o. | Inactive | |
| Zomepirac plus butorphanol 0.0195 mg/kg sc | | 2.0** |
| Butorphanol 0.0195 mg/kg sc** plus saline 5 ml/kg p.o. | Inactive | |

*Significantly different from zomepirac plus saline p <0.05.
**Estimated, see text.

The ratio of the calculated analgesic ED$_{50}$ for zomepirac sodium plus saline to the calculated ED$_{50}$ for zomepirac sodium plus butorphanol tartrate is used in the calculation of the dosage range of zomepirac sodium that would be employed when administered with a specified dosage range of butorphanol tartrate. This ratio will be referred to as the mouse potentiating factor, MPF.

Likewise, oral doses of butorphanol tartrate, 0.14, 0.25 and 0.44 mg/kg significantly lower the oral analgesic ED$_{50}$ of zomepirac sodium [Table II]. The first experiment conducted with an oral dose of 0.05 mg/kg of butorphanol tartrate and zomepirac sodium gave equivocal results. In a subsequent experiment no potentiation was observed, i.e., the two ED$_{50}$'s for zomepirac sodium were not significantly different one from the other. It is concluded that an oral dose of 0.05 mg/kg of butorphanol tartrate does not potentiate the oral analgesic potency of zomepirac sodium. A control experiment was also conducted. Mice were pretreated with saline in place of butorphanol tartrate and an oral ED$_{50}$ for zomepirac sodium determined. This oral ED$_{50}$ for zomepirac sodium was essentially identical with the control ED$_{50}$ for zomepirac sodium determined that same day. This observation further supports the claim for the potentiating effect of butorphanol tartrate, at specified doses, on the oral analgesic potency of zomepirac sodium.

The minimal oral dose of butorphanol tartrate that would be expected to significantly potentiate the oral analgesic potency of zomepirac sodium was estimated graphically. As can be seen from the data in Table II, the oral administration of 0.05 mg/kg of butorphanol tartrate did not result in a significant, p>0.05, increase in the potency of zomepirac sodium (potency increase 0.94 fold) and a significant, p>0.05, increase in the potency of zomepirac sodium was observed when a dose of 0.14 mg/kg of butorphanol tartrate was administered (3.71 fold increase). In view of the foregoing relationship, it is assumed that if the potency of zomepirac sodium were increased two-fold, the difference between the calculated ED$_{50}$ for zomepirac sodium plus saline and calculated ED$_{50}$ for zomepirac sodium plus butorphanol tartrate would be significant at the 5 percent level. The theoretical dose of butorphanol tartrate that would be expected to affect a significant increase in the potency of zomepirac sodium, two-fold increase, was estimated graphically from a plot of the potency increase of 0.94 and 3.71 versus the doses of butorphanol tartrate employed. The dose of butorphanol tartrate thus estimated is 0.085 mg/kg. Since the dose 0.14 mg/kg of butorphanol tartrate administered orally did not produce a significant analgesic effect when administered with saline it is also expected that the lower dose of 0.085 mg/kg would not produce a significant analgesic effect in this assay.

The ratio of the calculated analgesic ED$_{50}$ for zomepirac sodium plus saline to the calculated ED$_{50}$ for zomepirac sodium plus butorphanol tartrate is used in the calculation of the dosage range of zomepirac sodium that would be employed when administered with a specified dosage range of butorphanol tartrate. This ratio will be referred to as the mouse potentiating factor, MPF.

TABLE II

| Treatment | Zomepirac ED$_{50}$ (95% CL) mg/kg p.o. | Potency ratio |
|---|---|---|
| Zomepirac plus saline 5 ml/kg p.o. | 0.71 (0.55–0.90) | |
| Zomepirac plus butorphanol 0.44 mg/kg p.o. | 0.16 (0.07–0.37)* | 4.44 |
| Butorphanol 0.44 mg/kg p.o. plus saline 5 ml/kg p.o. | Inactive | |
| Zomepirac plus saline 5 ml/kg p.o. | 0.66 (0.51–0.85) | |
| Zomepirac plus butorphanol 0.25 mg/kg p.o. | 0.29 (0.17–0.52) | 2.28 |
| Burorphanol 0.25 mg/kg p.o. plus saline 5 ml/kg p.o. | Inactive | |
| Zomepirac plus saline 5 ml/kg p.o. | 0.63 (0.49–0.81) | |
| Zomepirac plus butorphanol 0.14 mg/kg p.o. | 0.17 (0.07–0.43)* | 3.71 |
| Butorphanol 0.14 mg/kg p.o. plus saline 5 ml/kg p.o. | Inactive | |
| Zomepirac plus saline 5 ml/kg p.o. | 0.67 (0.49–0.92) | |
| Zomepirac plus butorphanol 0.05 mg/kg p.o. | 0.30 (0.13–0.70) | 2.23 |
| Burorphanol 0.05 mg/kg p.o. plus saline 5 ml/kg p.o. | Inactive | |
| Zomepirac plus saline 5 ml/kg p.o. | 0.72 (0.52–0.99) | |
| Zomepirac plus butorphanol 0.05 mg/kg p.o. | 0.77 (0.54–1.08) | 0.94 |
| Butorphanol 0.05 mg/kg p.o. plus saline 5 ml/kg p.o. | Inactive | |
| Zomepirac plus saline 5 ml/kg p.o. | 0.65 (0.52–0.80) | |
| Zomepirac plus saline 5 ml/kg p.o. | 0.63 (0.51–0.79) | 1.03 |
| Zomepirac plus butorphanol 0.085 mg/kg p.o. | | 2.0** |
| Butorphanol 0.085 mg/kg p.o.** plus saline 5 ml/kg p.o. | Inactive | |

*Significantly different from zomepirac plus saline p <0.05.
**Estimated, see text.

The estimation of the dosage ranges of butorphanol tartrate and zomepirac sodium claimed for man was based on tests in mice and arrived at in the following manner.

A. The intramuscular dosage range for butorphanol tartrate in man is reported in the literature, i.e., *Physicians Desk Reference*, 34th Edition, 1980 to be 1–4 mg. The analgesic ED$_{50}$ for butorphanol tartrate using the analgesic assay described earlier is 0.10 mg/kg subcutaneously. It is assumed that the intramuscular ED$_{50}$ for butorphanol tartrate would be similar to the subcutaneous ED$_{50}$ presented above.

First, it is assumed that to find the lower end of the dosage range in man, the ED$_{50}$ for butorphanol tartrate, 0.1 mg/kg is equivalent to a dose of 1 mg in man which means that 0.0195 mg/kg, presented earlier as the minimal effective dose that would affect a significant increase in the analgesic potency of zomepirac sodium, is equal to $$\frac{0.0195 \text{ mg/kg}}{0.10 \text{ mg/kg}} \times 1.0 \text{ mg} = 0.195 \text{ mg}$$

and the dose of 0.05 mg/kg dose of butorphanol tartrate used in the mouse experiment [Table I] is equal to $$\frac{0.05 \text{ mg/kg}}{0.10 \text{ mg/kg}} \times 1.0 \text{ mg} = 0.50 \text{ mg}$$

Then, to find the upper end of the dosage range in man it is assumed that the ED$_{50}$ for butorphanol tartrate is equal to 4 mg. in man which means that 0.0195 mg/kg [Table I] is equivalent to $$\frac{0.0195 \text{ mg/kg}}{0.10 \text{ mg/kg}} \times 4 \text{ mg} = 0.78 \text{ mg}$$

and 0.05 mg/kg in the mouse experiment is equal to $$\frac{0.05 \text{ mg/kg}}{0.10 \text{ mg/kg}} \times 4 \text{ mg} = 2 \text{ mg}$$

Thus, the intramuscular dosage range of butorphanol tartrate that would be expected to potentiate the oral analgesic potency of zomepirac sodium in man would be from the lowest dosage above to the highest dosage above, i.e., 0.195–2 mg or, to translate this range into mg/kg the figure becomes 0.0028–0.029 mg/kg (calculation is based on average 70 kg individual which is customary pharmacological practice).

B. The analgesic dosage range from zomepirac sodium in man is reported in the literature [Cooper, S. A., J. Clin. Pharmacol., 20(4), Part 2, 230, 1980; Wallenstein, S. L. et al., ibid, 20(4), Part 2, 250, 1980] to be 25–200 mg.

Since butorphanol tartrate has been found to potentiate the analgesic potency of zomepirac sodium, the doses of zomepirac sodium that would be administered in combination with butorphanol tartrate would therefore be reduced in relationship to the potentiating effect of butorphanol tartrate. This new effective dosage range of zomepirac sodium was calculated in the following manner. Doses of 0.0195, estimated, and 0.025 mg/kg of butorphanol tartrate shown in Table I were found to increase the analgesic potency of zomepirac sodium MPF 2.0 and 2.61, respectively. Therefore, the dosage range of zomepirac sodium would be expected to be reduced as follows.

1/2.61×25 mg=9.6 mg

1/2.61×200 mg=76.6 mg

1/2.0×25 mg=12.5 mg

1/2.0×200 mg=100.0 mg

Thus, the dosage range of zomepirac sodium in man would be reduced from 25–200 mg for zomepirac sodium by itself to 9.6–100 mg or 0.140–1.43 mg/kg (calculation based on an average 70 kg individual which is customary pharmacological practice) when zomepirac sodium is administered with butorphanol tartrate in the dosage range previously described.

C. The oral analgesic dosage range for butorphanol tartrate in man is reported in the literature, i.e., Gilbert, M. M. et al., J. Int. Med. Res., 6, 14–23, 1978; and Levin, H. M. et al., ibid 6, 24–33, 1978 to be 4–16 mg. The analgesic ED$_{50}$ for butorphanol tartrate using the analgesic assay described earlier is 1.3 mg/kg, p.o.

First, it is assumed that to find the lower end of the dosage range in man, the ED$_{50}$ of butorphanol tartrate in the mouse, 1.3 mg/kg is equivalent to a dose of 4 mg in man, which means that 0.10 mg/kg presented earlier as the minimal effective dose that would affect a significant increase in the analgesic potency of zomepirac sodium is equal to $$\frac{0.1 \text{ mg/kg}}{1.3 \text{ mg/kg}} \times 4 \text{ mg} = 0.31 \text{ mg}$$

and the 0.44 mg/kg dose of butorphanol tartrate used in the mouse experiment [Table II] is equal to $$\frac{0.44 \text{ mg/kg}}{1.3 \text{ mg/kg}} \times 4 \text{ mg} = 1.354 \text{ mg}$$

Then, to find the upper end of the dosage range in man, it is assumed that the ED$_{50}$ for butorphanol tartrate is equal to 16 mg in man which means that 0.1 mg/kg (estimated Table II) is equivalent to $$\frac{0.1 \text{ mg/kg}}{1.3 \text{ mg/kg}} \times 16 \text{ mg} = 1.23 \text{ mg}$$

and 0.44 mg/kg in the mouse experiment is equal to $$\frac{0.44 \text{ mg/kg}}{1.3 \text{ mg/kg}} \times 16 \text{ mg} = 5.42 \text{ mg}$$

Thus, the oral dosage range of butorphanol tartrate that would be expected to potentiate the oral analgesic potency of zomepirac sodium in man would be from the lowest dosage above to the highest dosage above, i.e., 0.31–5.42 mg or, to translate this range into mg/kg the figure becomes 0.0044–0.0774 mg/kg (calculation based on an average 70 kg individual which is customary pharmacological practice).

D. The analgesic dosage range for zomepirac sodium in man is reported in the literature [Cooper, S. A., J. Clin. Pharmacol. 20(4), Part 2, 230, 1980, Wallenstein, S. L. et al., ibid 20(4), Part 2, 250, 1980] to be 25–200 mg.

Since butorphanol tartrate has been found to potentiate the analgesic potency of zomepirac sodium, the doses of zomepirac sodium that would be administered in combination with butorphanol tartrate would therefore be reduced in relationship to the potentiating effect of butorphanol tartrate. This new effective dosage range of zomepirac sodium was calculated in the following manner. Doses of 0.10 estimated and 0.44 mg/kg of butorphanol tartrate in the mouse experiment shown in Table II were found to increase the analgesic potency of zomepirac sodium MPF, 2.0 and 4.44, respectively. Therefore, the dosage range of zomepirac sodium would be expected to be reduced as follows:

$1/4.44 \times 25$ mg = 5.63 mg $1/4.44 \times 200$ mg = 45.05 mg $1/2.0 \times 25$ mg = 12.5 mg $1/2.0 \times 200$ mg = 100.0 mg Thus, the dosage range of zomepirac sodium in man would be reduced from 25–200 mg for zomepirac sodium by itself to 5.63–100 mg or 0.080–1.43 mg/kg (calculation based on an average 70 kg individual which is customary pharmacological practice) when zomepirac sodium is administered with butorphanol tartrate in the dosage range previously described.

The finding that butorphanol tartrate at nonanalgesic doses significantly potentiates the oral analgesic potency of zomepirac sodium when administered by two different routes of administration, clearly indicates that butorphanol tartrate potentiates the analgesic potency of zomepirac sodium.

I claim:

1. A method for producing analgesia which comprises administering to a subject suffering from pain
   (1) as a primary agent from about 0.140 to 1.43 mg/kg of body weight of zomepirac or a pharmaceutically acceptable salt thereof, and
   (2) as potentiating agent from about 0.0028 to 0.029 mg/kg of body weight of butorphanol or a pharmaceutically acceptable salt thereof,
   said primary agent being administered orally, and said potentiating agent being administered parenterally, either simultaneously or sequentially.

2. A method for producing analgesia which comprises administering to a subject suffering from pain
   (1) as a primary agent from about 9.6 to 100 milligrams of zomepirac or a pharmaceutically acceptable salt thereof, and
   (2) as potentiating agent from about 0.195 to 2.0 milligrams of butorphanol or a pharmaceutically acceptable salt thereof,
   said primary agent being administered orally and said potentiating agent being administered parenterally, either simultaneously or sequentially.

3. A method for producing analgesia which comprises administering orally to a subject suffering from pain
   (1) as primary agent from about 0.080 to 1.43 mg/kg of body weight of zomepirac or a pharmaceutically acceptable salt thereof, and
   (2) as potentiating agent from about 0.0044 to 0.0774 mg/kg of body weight of butorphanol or a pharmaceutically acceptable salt thereof.

4. A method for producing analgesias which comprises orally administering to a subject suffering from pain
   (1) as primary agent from about 5.63 to 100 milligrams of zomepirac or a pharmaceutically acceptable salt thereof, and
   (2) as potentiating agent from about 0.31 to 5.42 milligrams of butorphanol or a pharmaceutically acceptable salt thereof.

5. A pharmaceutical composition suitable for reducing pain in dosage unit form comprising an effective antinociceptive amount in combination of
   (1) as primary agent from about 5.63 to 100 milligrams of zomepirac or a pharmaceutically acceptable salt thereof, and
   (2) as potentiating agent, from about 0.31 to 5.42 milligrams of butorphanol or a pharmaceutically acceptable salt thereof,
   wherein said primary and said potentiating agents are in admixture with a pharmaceutically acceptable carrier.

6. A composition according to claim 5 in which the primary active agent is zomepirac sodium.

7. A composition according to claim 5 in which the potentiating agent is butorphanol tartrate.

* * * * *